(12) United States Patent
Shikhman et al.

(10) Patent No.: US 8,758,370 B2
(45) Date of Patent: *Jun. 24, 2014

(54) SUTURE LOADING ASSEMBLY

(75) Inventors: Oleg Shikhman, Trumbull, CT (US); Paul A. Scirica, Huntington, CT (US)

(73) Assignee: Interventional Therapies, LLC, Westport, CT (US)

( * ) Notice: Subject to any disclaimer, the term of this patent is extended or adjusted under 35 U.S.C. 154(b) by 1712 days.

This patent is subject to a terminal disclaimer.

(21) Appl. No.: 10/726,031

(22) Filed: Dec. 1, 2003

(65) Prior Publication Data

US 2004/0097968 A1 May 20, 2004

Related U.S. Application Data

(62) Division of application No. 10/037,899, filed on Oct. 22, 2001, now abandoned.

(51) Int. Cl.
*A61B 17/04* (2006.01)

(52) U.S. Cl.
CPC ......... *A61B 17/0485* (2013.01); *A61B 17/0487* (2013.01); *A61B 17/0467* (2013.01)
USPC .......................................... 606/148; 606/144

(58) Field of Classification Search
CPC ........... A61B 17/0467; A61B 17/0469; A61B 17/0485; A61B 17/0487; D05B 87/00; D05B 87/02
USPC ......... 606/151–158, 213, 217, 228–232, 110, 606/113, 127, 139, 144, 148, 222–223, 114, 606/128, 45, 46; 600/104, 106, 107; 223/99
See application file for complete search history.

(56) References Cited

U.S. PATENT DOCUMENTS

| | | | |
|---|---|---|---|
| 2,092,929 A | | 9/1937 | Ovington |
| 3,361,382 A | * | 1/1968 | Converse ................... 242/137.1 |
| 3,612,050 A | | 10/1971 | Sheridan |
| 3,802,438 A | | 4/1974 | Wolvek |
| 3,901,244 A | | 8/1975 | Schweizer |
| 3,929,123 A | | 12/1975 | Jamshidi |
| 4,102,478 A | * | 7/1978 | Samoilov ......................... 223/99 |
| 4,134,406 A | * | 1/1979 | Iglesias ........................... 606/46 |
| 4,662,068 A | | 5/1987 | Polonsky |
| 4,667,684 A | | 5/1987 | Leigh |
| 4,719,713 A | | 1/1988 | Hagle |
| 4,779,616 A | * | 10/1988 | Johnson ......................... 606/148 |

(Continued)

FOREIGN PATENT DOCUMENTS

CA 667514 7/1963
WO WO0135833 5/2001

OTHER PUBLICATIONS

Application No. 200880014925.4 First Office Action dated Aug. 12, 2010, 10 pages.

(Continued)

*Primary Examiner* — Kathleen Holwerda
(74) *Attorney, Agent, or Firm* — Cantor Colburn LLP

(57) ABSTRACT

A suture loading assembly for threading suture material through a device comprises a body, an attaching member extending from the body for attaching the body to the device, and a flexible loop extending from a distal end of the body and threadable through a ferrule in the distal end of the device.

21 Claims, 18 Drawing Sheets

(56) References Cited

U.S. PATENT DOCUMENTS

| | | | |
|---|---|---|---|
| 4,852,568 A | 8/1989 | Kensey | |
| 4,890,612 A | 1/1990 | Kensey | |
| 4,892,098 A | 1/1990 | Sauer | |
| 4,917,082 A * | 4/1990 | Grossi et al. | 606/46 |
| 4,929,240 A | 5/1990 | Kirsch et al. | |
| 5,137,198 A | 8/1992 | Nobis et al. | |
| 5,211,644 A | 5/1993 | VanBeek et al. | |
| 5,242,459 A | 9/1993 | Buelna | |
| 5,261,918 A | 11/1993 | Phillips et al. | |
| 5,304,184 A | 4/1994 | Hathaway et al. | |
| 5,306,280 A | 4/1994 | Bregen et al. | |
| 5,336,229 A | 8/1994 | Noda | |
| 5,342,393 A | 8/1994 | Stack | |
| 5,368,601 A | 11/1994 | Sauer et al. | |
| 5,370,660 A | 12/1994 | Weinstein et al. | |
| 5,380,290 A | 1/1995 | Makower et al. | |
| 5,382,254 A | 1/1995 | McGarry et al. | |
| 5,383,901 A | 1/1995 | McGregor et al. | |
| 5,391,183 A | 2/1995 | Janzen et al. | |
| 5,405,354 A | 4/1995 | Sarrett | |
| 5,409,478 A | 4/1995 | Gerry et al. | |
| 5,411,520 A | 5/1995 | Nash et al. | |
| 5,417,699 A | 5/1995 | Klein et al. | |
| 5,417,700 A | 5/1995 | Egan | |
| 5,423,830 A * | 6/1995 | Schneebaum et al. | 606/115 |
| 5,425,737 A | 6/1995 | Burbank et al. | |
| 5,425,745 A | 6/1995 | Green et al. | |
| 5,431,666 A | 7/1995 | Sauer et al. | |
| 5,437,665 A * | 8/1995 | Munro | 606/47 |
| 5,454,822 A | 10/1995 | Schob et al. | |
| 5,466,241 A * | 11/1995 | Leroy et al. | 606/139 |
| 5,476,470 A | 12/1995 | Fitzgibbons, Jr. | |
| 5,478,003 A | 12/1995 | Green et al. | |
| 5,486,186 A | 1/1996 | Yoon | |
| 5,501,692 A * | 3/1996 | Riza | 606/148 |
| 5,520,702 A * | 5/1996 | Sauer et al. | 606/144 |
| 5,527,319 A | 6/1996 | Green et al. | |
| 5,527,322 A | 6/1996 | Klein et al. | |
| 5,533,987 A | 7/1996 | Pray et al. | |
| 5,540,698 A | 7/1996 | Preissman | |
| 5,554,169 A | 9/1996 | Green et al. | |
| 5,562,664 A * | 10/1996 | Durlacher et al. | 606/96 |
| 5,562,685 A | 10/1996 | Mollenauer et al. | |
| 5,562,686 A | 10/1996 | Sauer et al. | |
| 5,575,800 A | 11/1996 | Gordon | |
| 5,575,801 A * | 11/1996 | Habermeyer et al. | 606/148 |
| 5,578,057 A | 11/1996 | Wenstrom, Jr. | |
| 5,586,986 A | 12/1996 | Hinchliffe | |
| 5,591,177 A | 1/1997 | Lehrer | |
| 5,643,289 A * | 7/1997 | Sauer et al. | 606/139 |
| 5,665,105 A | 9/1997 | Furnish et al. | |
| 5,669,917 A | 9/1997 | Sauer et al. | |
| 5,676,689 A | 10/1997 | Kensey et al. | |
| 5,700,273 A | 12/1997 | Buelna et al. | |
| 5,704,973 A | 1/1998 | Sakurada et al. | |
| 5,718,714 A | 2/1998 | Livneh | |
| 5,725,536 A | 3/1998 | Oberlin et al. | |
| 5,752,964 A | 5/1998 | Mericle | |
| 5,766,183 A | 6/1998 | Sauer | |
| 5,772,663 A | 6/1998 | Whiteside et al. | |
| 5,782,844 A | 7/1998 | Yoon et al. | |
| 5,792,152 A | 8/1998 | Klein et al. | |
| 5,792,153 A | 8/1998 | Swain et al. | |
| 5,797,927 A | 8/1998 | Yoon | |
| 5,800,447 A * | 9/1998 | Wenstrom, Jr. | 606/139 |
| 5,810,849 A | 9/1998 | Kontos | |
| 5,814,065 A | 9/1998 | Diaz | |
| 5,830,125 A | 11/1998 | Scribner et al. | |
| 5,836,955 A | 11/1998 | Buelna et al. | |
| 5,836,956 A | 11/1998 | Buelna et al. | |
| 5,839,639 A | 11/1998 | Sauer et al. | |
| 5,855,585 A | 1/1999 | Kontos | |
| 5,935,149 A * | 8/1999 | Ek | 606/232 |
| 5,938,668 A | 8/1999 | Scirica et al. | |
| 5,997,555 A | 12/1999 | Kontos | |
| 6,036,699 A | 3/2000 | Andreas et al. | |
| 6,045,560 A | 4/2000 | McKean et al. | |
| 6,048,358 A | 4/2000 | Barak | |
| 6,056,771 A | 5/2000 | Proto | |
| 6,066,144 A | 5/2000 | Wolf et al. | |
| 6,068,648 A | 5/2000 | Cole et al. | |
| 6,099,553 A | 8/2000 | Hart et al. | |
| 6,117,144 A | 9/2000 | Nobles et al. | |
| 6,136,010 A | 10/2000 | Modesitt et al. | |
| 6,206,893 B1 | 3/2001 | Klein et al. | |
| 6,217,592 B1 | 4/2001 | Freda et al. | |
| 6,221,084 B1 | 4/2001 | Fleenor | |
| 6,254,620 B1 | 7/2001 | Koh et al. | |
| 6,368,334 B1 | 4/2002 | Sauer | |
| 6,398,796 B2 | 6/2002 | Levinson | |
| 6,428,549 B1 | 8/2002 | Kontos | |
| 6,436,109 B1 | 8/2002 | Kontos | |
| 6,451,031 B1 | 9/2002 | Kontos | |
| 6,454,777 B1 | 9/2002 | Green | |
| 6,511,489 B2 | 1/2003 | Field et al. | |
| 6,514,263 B1 | 2/2003 | Stefanchik et al. | |
| 6,517,553 B2 | 2/2003 | Klein et al. | |
| 6,533,796 B1 | 3/2003 | Sauer et al. | |
| 6,569,187 B1 | 5/2003 | Bonutti et al. | |
| 6,641,592 B1 | 11/2003 | Sauer et al. | |
| 6,830,174 B2 | 12/2004 | Hillstead et al. | |
| 6,997,931 B2 | 2/2006 | Sauer et al. | |
| 7,037,315 B2 | 5/2006 | Sancoff et al. | |
| 2002/0099389 A1 | 7/2002 | Michler et al. | |
| 2002/0177860 A1 | 11/2002 | Nicholas et al. | |
| 2003/0040760 A1 | 2/2003 | Hnojewyj et al. | |
| 2003/0050650 A1 | 3/2003 | Field et al. | |
| 2003/0204205 A1 | 10/2003 | Sauer et al. | |
| 2004/0068272 A1 | 4/2004 | Sauer et al. | |
| 2008/0082123 A1 | 4/2008 | Forsberg et al. | |
| 2010/0217311 A1 | 8/2010 | Jenson et al. | |

OTHER PUBLICATIONS

Application No. 200880014925.4 Second Office Action dated Jun. 15, 2011, 6 pages.

International Search Report for PCT/US02/33747 dated Mar. 7, 2003, 3 pages.

International Search Report for PCT/US2008/059551 dated Sep. 25, 2008, 8 pages.

International Search Report and Written Opinin for PCT/US2010/039328 dated Feb. 8, 2011, 16 pages.

China Application No. 200880014925.4 Third Office Action dated Nov. 9, 2011, 5 pages.

Supplemental European Search Report for PCT/US0233747 dated Feb. 26, 2008, 5 pages.

* cited by examiner

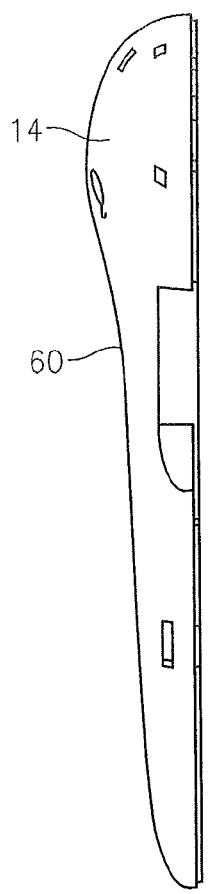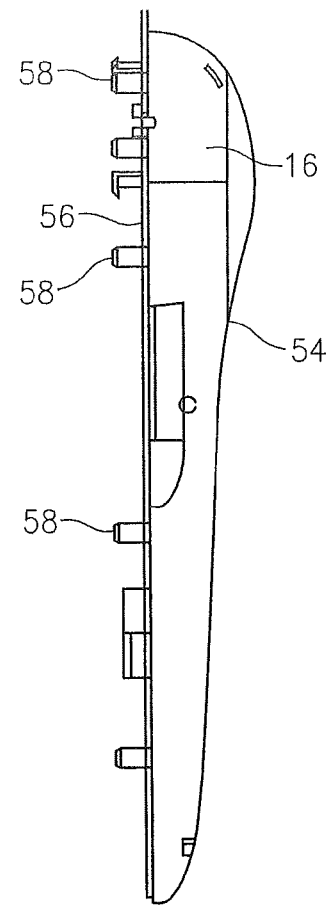
FIG. 4   FIG. 5
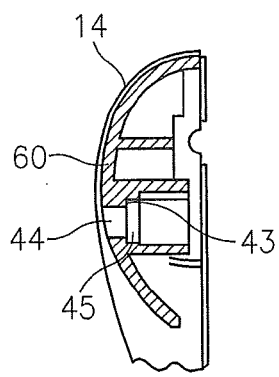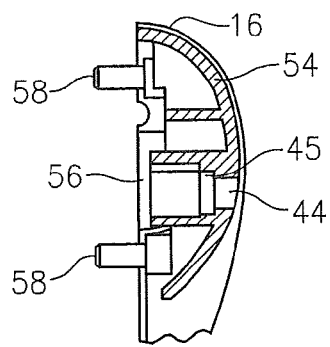
FIG. 6   FIG. 7

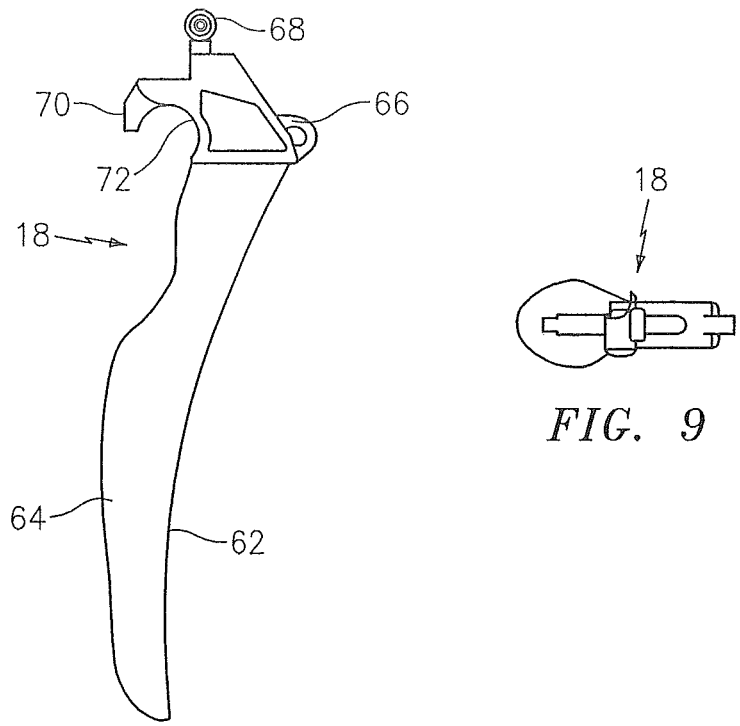
FIG. 8
FIG. 9
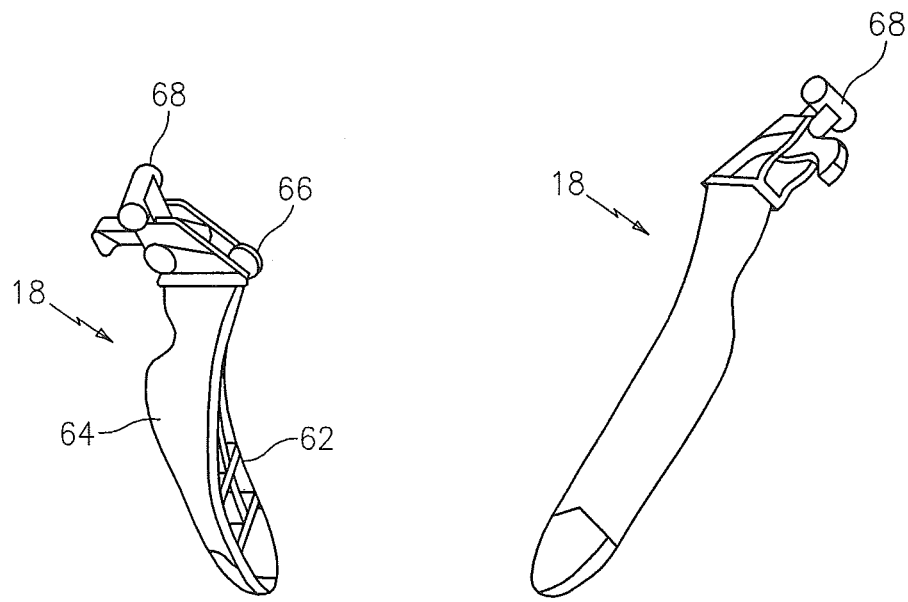
FIG. 10
FIG. 11

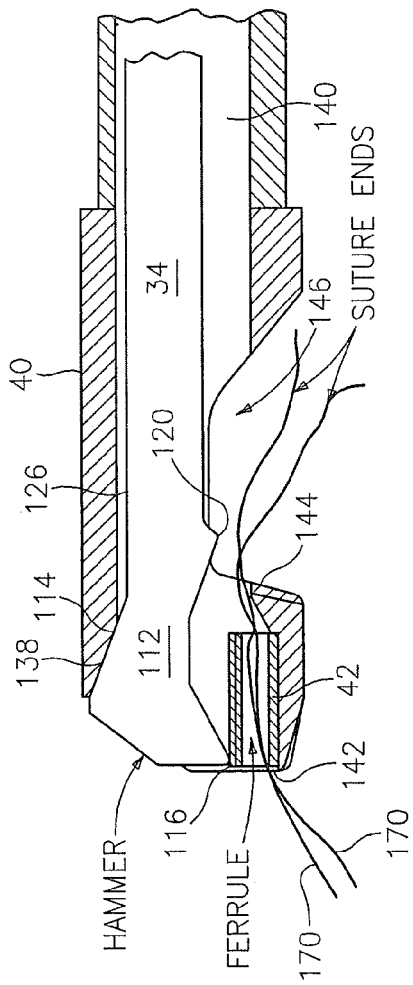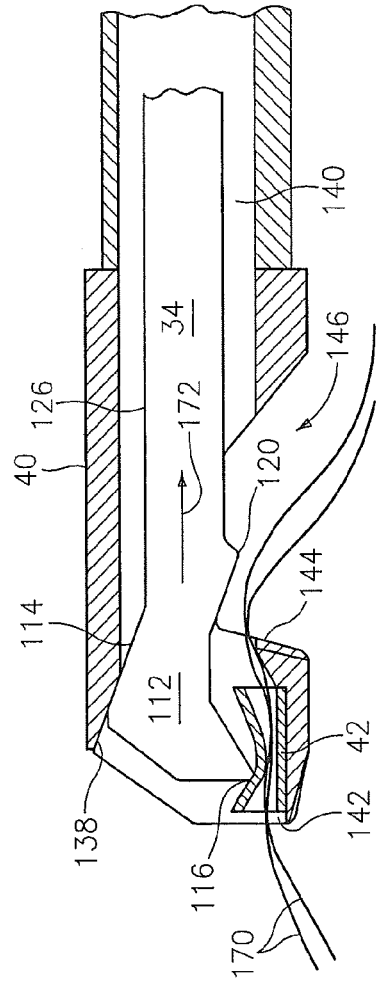

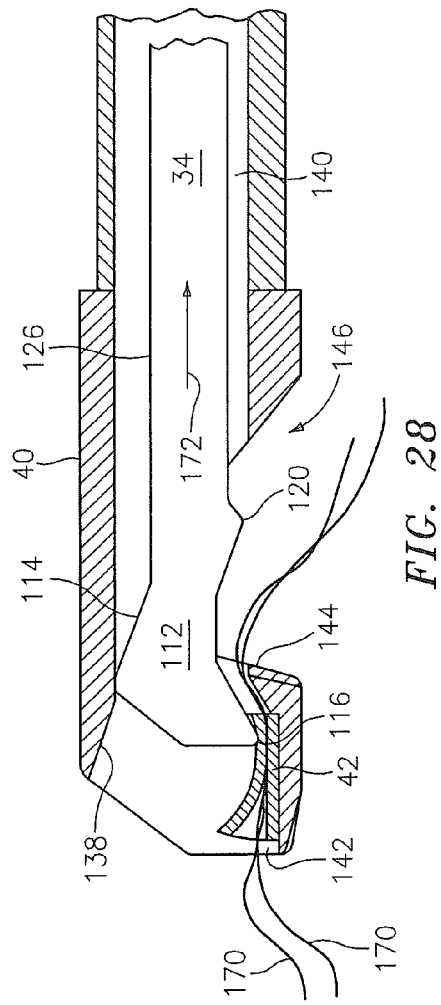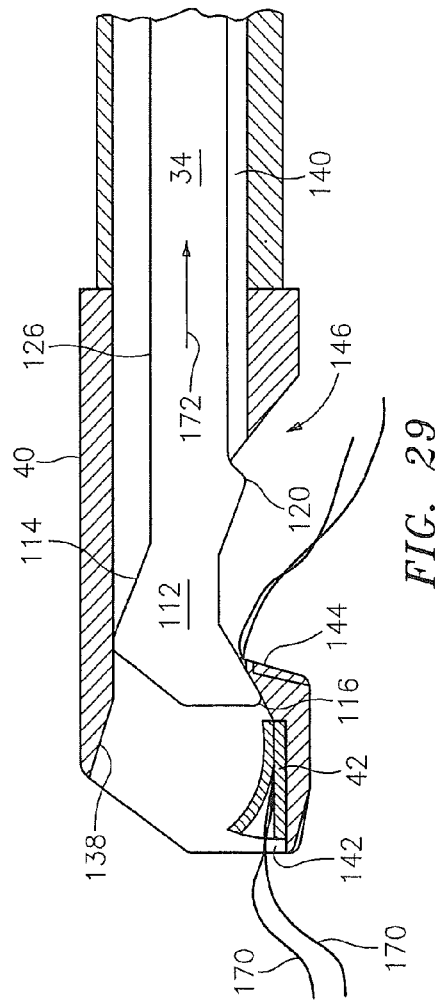

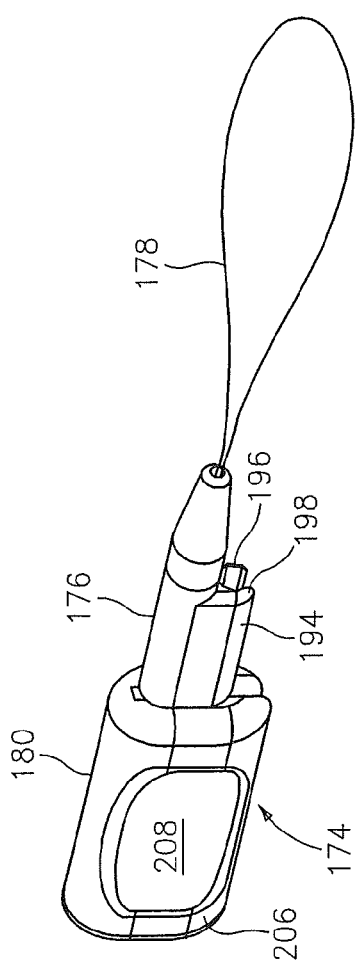
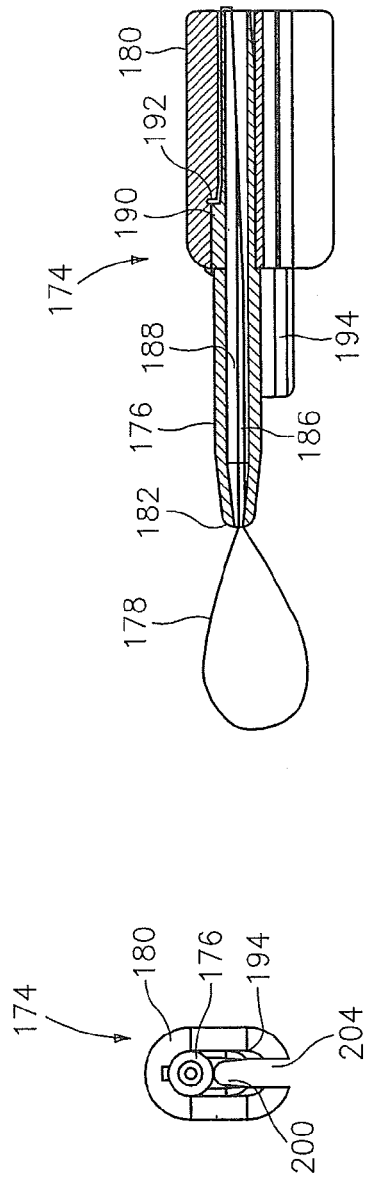
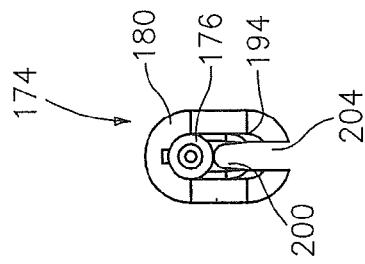

SUTURE LOADING ASSEMBLY

CROSS REFERENCE TO RELATED APPLICATIONS

The present application is a divisional of U.S. patent application Ser. No. 10/037,899, filed Oct. 22, 2001, now abandoned, the entire contents of which are specifically incorporated herein by reference.

BACKGROUND

The present disclosure relates to an instrument and a method for closing a hole or puncture in a blood vessel. More particularly, this disclosure relates to a handle assembly for a surgical instrument.

When performing catheterization procedures, such an angiography or angioplasty, a catheter is generally introduced into the vascular system by first penetrating the skin, underlying muscle tissue and blood vessel with a sharpened hollow needle. Next, a guide wire is commonly inserted through the lumen of the hollow needle and is caused to enter the selected blood vessel. Subsequently, the needle is typically slid off the guide wire and a combination of a dilator and an introducer (or an introducer alone) are fed over the guide wire and pushed through the skin to enter the vessel. The guide wire can then be removed and the desired catheter to carry out the procedure is fed through the lumen of the introducer and advanced through the vascular system until the working end of the catheter is appropriately positioned. Following the conclusion of the catheterization procedure, the working catheter will be withdrawn and, subsequently, the dilator and/or introducer will also be removed from the wound.

At this point in the procedure, the vessel leakage must be controlled in order to stem the flow of blood through the puncture. Because it is common practice to administer a blood thinning agent to the patient prior to many of the catheterization procedures, stemming the blood flow can be troublesome. A common method of sealing the wound is to maintain external pressure over the vessel until the puncture naturally seals. This method of puncture closure typically takes about thirty minutes, with the length of time usually being greater if the patient is hypertensive or anti-coagulated. In some anti-coagulated patients, the introducer is left in place for hours to allow the anti-coagulant to wear off. When human hand pressure is utilized, it can be uncomfortable for the patient and can use costly professional time on the part of the hospital staff. Other pressure techniques, such as pressure bandages, sandbags or clamps, have been employed, but these devices also require the patient to remain motionless for an extended period of time and the patient must be closely monitored to ensure their effectiveness.

Suture securing instruments are being developed to assist in finalizing the suturing procedure, however some of these instruments leave behind crimped securing members with sharp edges, or require a separate step to be performed to cut the suture material after the securing member has been crimped.

SUMMARY

The above discussed and other drawbacks and deficiencies are overcome or alleviated by a surgical instrument, including a suture loading assembly for threading suture material through the device. The suture loading assembly comprises a body, an attaching member extending from the body for attaching the body to the device, and a flexible loop extending from a distal end of the body and threadable through a ferrule in the distal end of the device.

The above-discussed and other features and advantages of the present invention will be appreciated and understood by those skilled in the art from the following detailed description and drawings.

BRIEF DESCRIPTION OF THE DRAWINGS

Referring to the FIGURES wherein like elements are numbered alike in the several FIGURES:

FIG. 4 shows a proximal plan view of a side of the handle assembly for the cutting and crimping device of FIG. 1;

FIG. 5 shows a proximal plan view of another side of the handle assembly for the cutting and crimping device of FIG. 1;

FIG. 6 shows a partial cross-sectional view of the side of FIG. 4;

FIG. 7 shows a partial cross-sectional view of the side of FIG. 5 taken along line 7-7 of FIG. 3;

FIG. 8 shows a side plan view of the trigger of the handle assembly for the cutting and crimping device of FIG. 1;

FIG. 9 shows a top plan view of the trigger of FIG. 8;

FIG. 10 shows proximal perspective view of the trigger of FIG. 8;

FIG. 11 shows a distal perspective view of the trigger of FIG. 8;

FIG. 26 shows a partial side cross-sectional view of the cutting and crimping device of FIG. 1 in an initial stage of securing suture material;

FIG. 27 shows a partial side cross-sectional view of the cutting and crimping device of FIG. 1 in an advanced stage of securing suture material;

FIG. 28 shows a partial side cross-sectional view of the cutting and crimping device of FIG. 1 in a further advanced stage of securing suture material;

FIG. 29 shows a partial side cross-sectional view of the cutting and crimping device of FIG. 1 in a final stage of securing suture material;

FIG. 30 shows a perspective view of one embodiment of a suture loading assembly;

FIG. 31 shows a side cross-sectional view of the suture loading assembly of FIG. 30;

FIG. 32 shows a front plan view of the suture loading assembly of FIG. 30;

DETAILED DESCRIPTION

Figure 1:
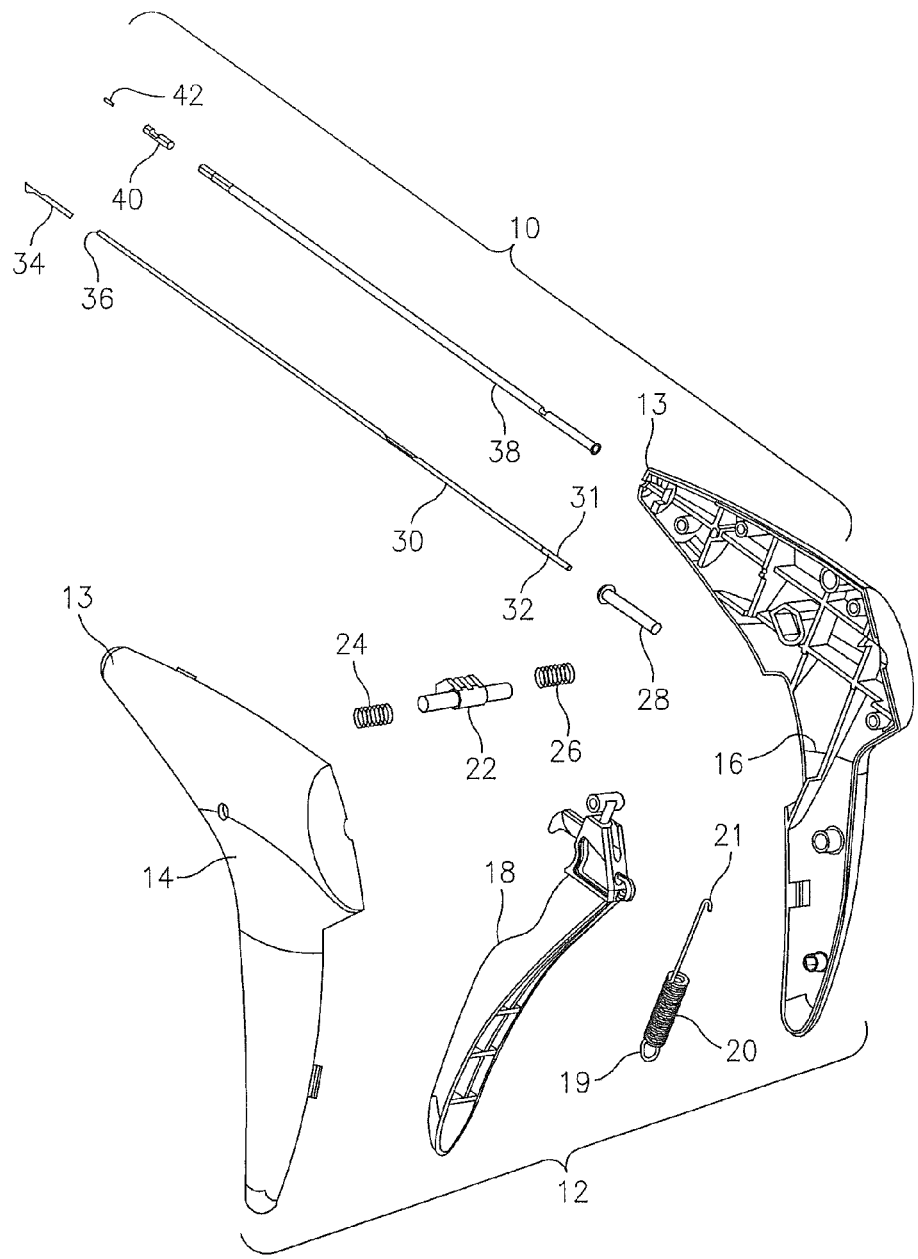
FIG. 1 shows an exploded perspective view of the cutting and crimping device.

Referring to FIG. 1, a crimping and cutting device 10 is shown for applying a ferrule around suture material after it has been applied to body tissue by a suturing apparatus, or by any other suturing procedure in which suture material is used, in order to secure the suture.

In general, device 10 preferably includes a handle assembly 12. The handle assembly may include first and second sides 14, 16 and a trigger member 18 with an associated spring 20 for the trigger return. The handle assembly 12 further preferably includes a safety button 22 which is centrally biased by springs 24, 26 and which must be depressed before trigger actuation will be permitted. Also preferably within the handle assembly 12 is an adjustment screw 28 which facilitates ferrule loading by the manufacturer. The adjustment screw is connected to a proximal end 32 of a central rod 30, which extends from a distal end 13 of the handle assembly 12. A hammer element 34 is connected to the distal end 36 of the central rod 30. Surrounding the central rod 30 is a tubular portion 38 which also extends from a distal end 13 of the handle assembly 12. A tip 40 is secured to the proximal end of the tubular portion 38. Positioned within the tip 40 is a ferrule 42.

Figure 2:
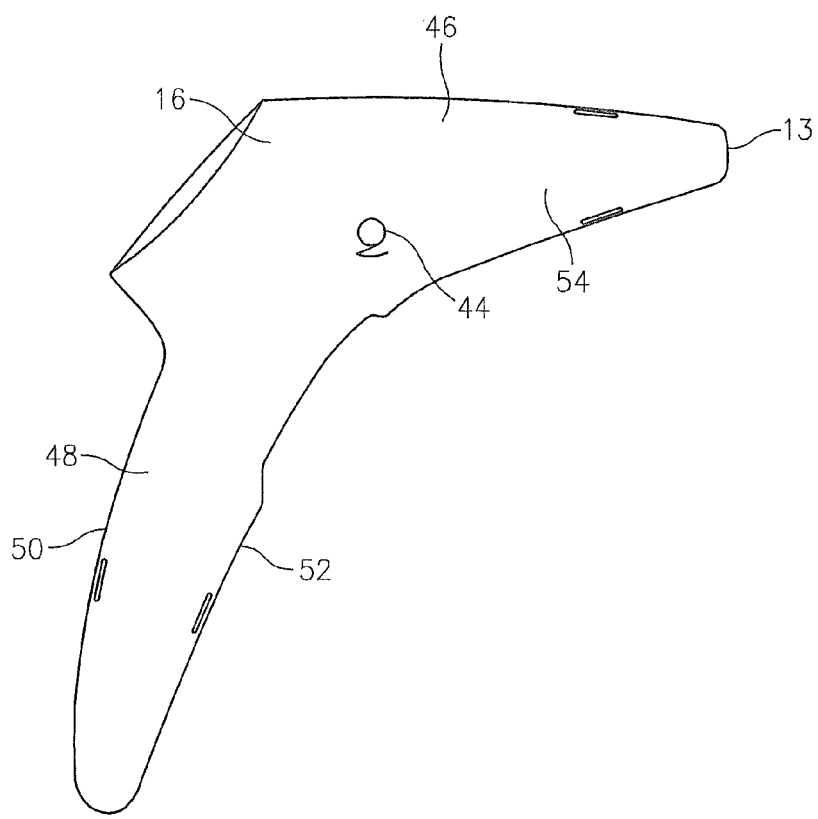
FIG. 2 shows a side plan view of an exterior of the handle assembly for the cutting and crimping device of FIG. 1.
Figure 3:
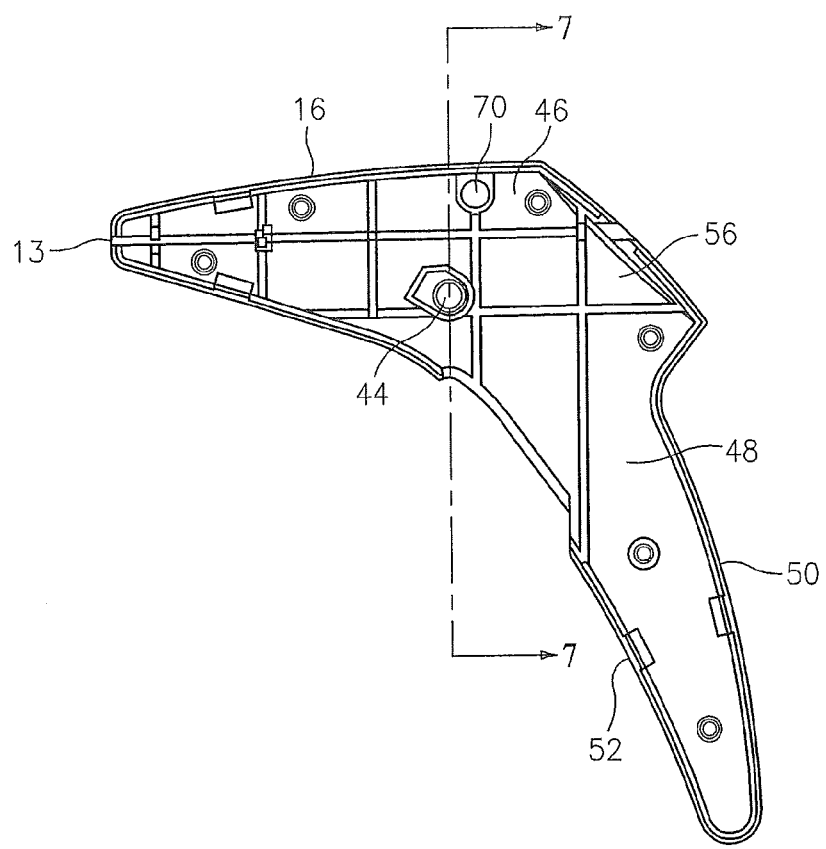
FIG. 3 shows an interior plan view of a side of the handle assembly for the cutting and crimping device of FIG. 1.

An exterior 54 of side 16 of handle assembly 12 is shown in FIG. 2 and FIG. 3 shows an interior 56 of side 16, similar to that shown in FIG. 1. The handle assembly 12 includes a distal end 13 from which the central rod 30 and tubular portion 38 extend. The side 16 includes an opening 44 through which a portion of the safety button 22 extends, as will be further described. The side 16, as with the side 14, preferably includes a body portion 46 and a grasping portion 48. The body portion 46 houses the safety button 22 and the adjustment screw 28 and includes the connections for the central rod 30, tubular portion 38, and trigger 18. The grasping portion 48, on the hand, preferably includes an ergonomically shaped grip for an operator. The grasping portion 48 includes an outward surface 50 and an inward surface 52. The inward surface 52 faces an inner surface of the trigger 18.

As shown in FIGS. 4 and 5, the interior 56 of side 16 is shown to include protrusions 58 which mate with corresponding shaped recesses (not shown) within the interior of side 14 during manufacture. Alternatively, the protrusions 58 could be located on side 14 with recesses within interior 56, or some of the protrusions 58 could be located on both sides 14 and 16 with corresponding recesses oppositely positioned on sides 14 and 16. When assembled, an exterior 60 of the side 14 and the exterior 54 of side 16 preferably combine to form a smooth outer surface of the handle assembly 12 for gripping by the operator.

Turning now to FIGS. 6 and 7, a cross-section of the sides 14 and 16 is shown. Specifically, a cross-section of side 16 taken along line 7-7 within FIG. 3 is shown in FIG. 7. A cross-section of side 14 taken along the same location, that is, through the opening 44 for safety button 22, is shown in FIG. 6. The opening 44 extends from the exterior 54 of side 16 to the exterior 60 of side 14. Thus, the safety button, as will be further described below, is accessible from either side 14 or 16 of the handle assembly 12.

Turning now to FIGS. 8-11, the trigger 18 is shown to include an inner surface 62 which, when assembled within the handle assembly 12, faces the inward surface 52 of the sides 14 and 16. Outer surface 64 is preferably smooth for grasping by an operator. The trigger 18 may include spring receiving member 66 for receiving a hook 21 (as shown in FIG. 1) of the spring 20. As shown, the spring receiving member 66 is an opening, although other shapes, such as a hook shape would be within the scope of this invention. With the hook 21 of the spring 20 engaged within the spring receiving member 66 of the trigger 18 and a securing member 19 (FIG. 1) of spring 20 securing the spring 20 to a protrusion 58 on side 16, the trigger 18 must expand the spring 20 when the inner surface 62 of the trigger 18 is compressed towards the inward surface 52 of the sides 14, 16. The spring 20 thus biases the trigger 18 in an "open" or "unsqueezed" configuration. That is, after the trigger 18 is squeezed, the spring 20 will return the trigger 18 to its original position when pressure on the trigger 18 is removed.

The trigger 18 further preferably includes a pivot rod 68 for pivotally securing the trigger 18 within the handle assembly 12, such as within opening 70 within interior 56 of side 16, as shown in FIG. 3. Thus, when the trigger 18 is squeezed, it will pivot about the longitudinal axis of pivot rod 68 located within the sides 14, 16.

The trigger 18 further preferably includes a hook-shaped safety button engaging member 70 which includes an inner receiving pocket 72 which either hovers above or rests upon the safety button 22 or is received within one of the grooves of the safety button 22, as will be further described with reference to FIGS. 12-13.

Figure 12:
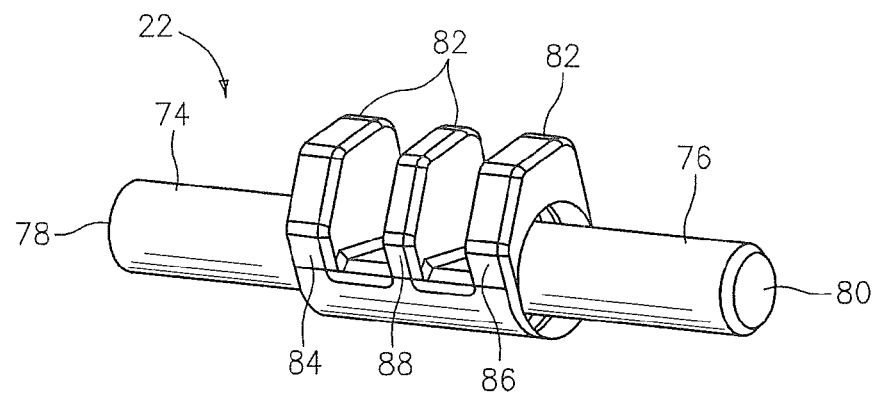
FIG. 12 shows a perspective view of the safety button of the handle assembly for the cutting and crimping device of FIG. 1.
Figure 13:
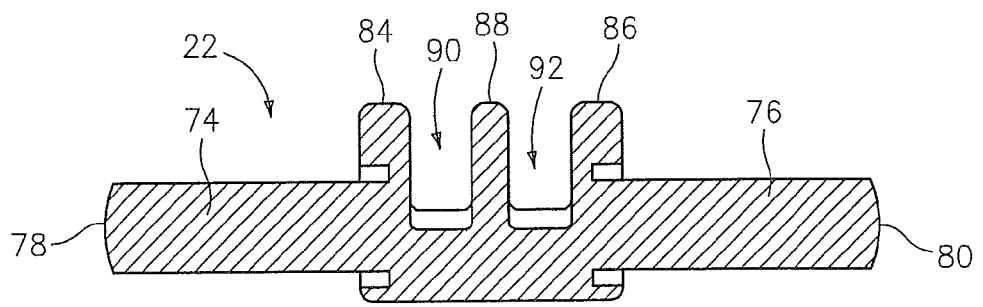
FIG. 13 shows a cross-sectional view of the safety button of FIG. 12.

Turning now to FIGS. 12-13, the safety button 22 preferably includes a pair of pins 74, 76. Each of the pins 74, 76 include an engageable end 78, 80, respectively, which protrude through the openings 44 of the sides 14, 16 and are accessible by the operator. Surrounding the pins 74, 76, respectively, are the springs 24, 26. The springs 24, 26 are seated within pockets 45 (FIGS. 6 and 7) of the openings 44. The pockets 45 have a slightly larger diameter than the exterior most openings 44 such that the springs 24, 26 received therein abut against a wall 43 within the pockets 45. The safety button 22 further preferably includes three ribs, shown collectively as ribs 82. The ribs 82 include a first side rib 84, a second side rib 86, and a middle rib 88. A first side gap 90 is created between the first side rib 84 and the middle rib 88 and a second side gap 92 is created between the second side rib 86 and the middle rib 88.

When assembled within the handle assembly 12, the safety button 22 is preferably centrally located, and spring biased to be centrally located, within the handle assembly 12 such that the safety button engaging member 70 of the trigger 18 abuts with the middle rib 88 when an attempt to squeeze the trigger 18 is made. However, when the engageable end 78 of the safety button 22 is depressed by an operator, the safety button 22 moves within the handle assembly 12 such that the safety button engaging member 70 of the trigger 18 will fall into the gap 90. Thus, the trigger 18 is now free to be squeezed by the operator. Likewise, when the engageable end 80 of the safety button 22 is depressed by an operator, the safety button 22 moves within the handle assembly 12 such that the safety button engaging member 70 of the trigger 18 will fall into the gap 92 freeing the trigger 18 to be moved by the operator. While the accessibility of the safety button 22 from either side 14 or 16 of the handle assembly 12 provides ease of use to the operator, it is within the scope of this invention to have the safety button accessible from only one side 14 or 16 of the handle assembly 12, which would thus require only one gap and only one pair of ribs in the safety button 22. Pressing the safety button 22 will preferably allow the safety button engaging member 70 to be retained between two adjacent ribs, i.e. ribs 84 and 88 or ribs 88 and 86, but with enough space within either gap 90 or 92 to allow movement of the safety button engaging member 70 during a squeeze of the trigger 18. The purpose of the safety button 22 is to prevent unintentional accidental firing of the device 10. Thus, preferably the safety button 22 is self-centering due to springs 24, 26. After depressing the safety button 22 and releasing the trigger 18 for movement, and after the trigger 18 is squeezed and released by the operator, the safety button 22 will preferably return to its center position, re-locking the trigger 18 from movement. Preferably, the device 10 is a one-time use instrument such that a ferrule 42 cannot be reloaded within the device.

Figure 14:
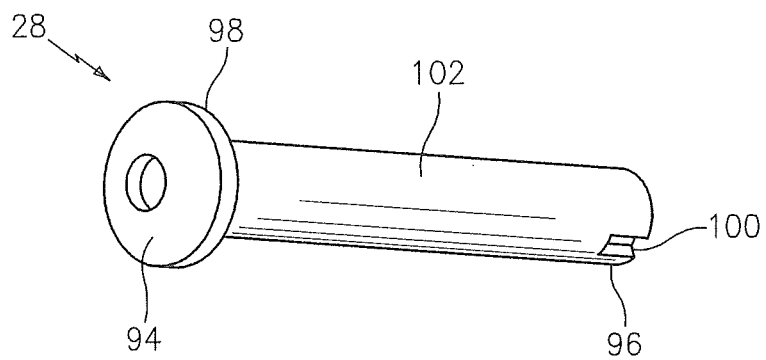
FIG. 14 shows a perspective view of the adjustment screw of the handle assembly for the cutting and crimping device of FIG. 1.
Figure 15:
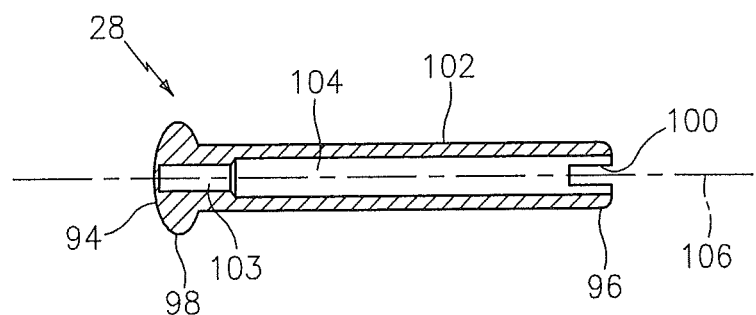
FIG. 15 shows a cross-sectional view of the adjustment screw of FIG. 14.

Turning now to FIGS. 14 and 15, and as additionally shown in FIG. 1, the adjustment screw 28 is shown which facilitates ferrule loading by the manufacturer. The adjustment screw 28 preferably includes a distal end 94 and a proximal end 96'. The distal end 94 may include a bulbous or larger diametered head 98. The proximal end 96 may include a slotted portion 100. A shaft 102 preferably connects the distal end 94 to the proximal end 96. Extending within the adjust screw 28 is a longitudinal bore 104 which extends along the longitudinal axis 106. The bore 104 may have a smaller inner diameter 103 within the head 98 than within the shaft 102. As demonstrated in FIG. 1, the adjustment screw 28 is connected to a proximal end 32 of the central rod 30, which extends from a distal end 13 of the handle assembly 12. The adjustment screw 28 is preferably completely contained within the handle assembly 12 and is not accessible by the operator. During assembly, the adjustment screw 28 accepts the section 31, preferably threaded, of the proximal end 32 of the central rod 30 so that the length of the central rod 30 may be properly adjusted with respect to the tubular portion 38. The smaller inner diameter 103 is also preferably threaded such that the inner diameter 103 may be threaded to mate with threads on section 31 of rod 30. Turning the adjustment screw 28 after loading the ferrule 42 shortens the rod 30 and allows the distal end 108 of the hammer element 34 to retain the ferrule 42 in the ferrule accepting opening 142 in the tip 40. That is, the proper length of the central rod 30 with respect to the tubular portion 38 helps ensure that the ferrule 42 is retained within the distal end of the device 10. Also, the ability to correct the length of the central rod 30 using the adjustment screw 28 eliminates the need to require very tight tolerances during manufacture of the central rod 30, thus easing the manufacturing process of the device 10.

Figures 16, 17:
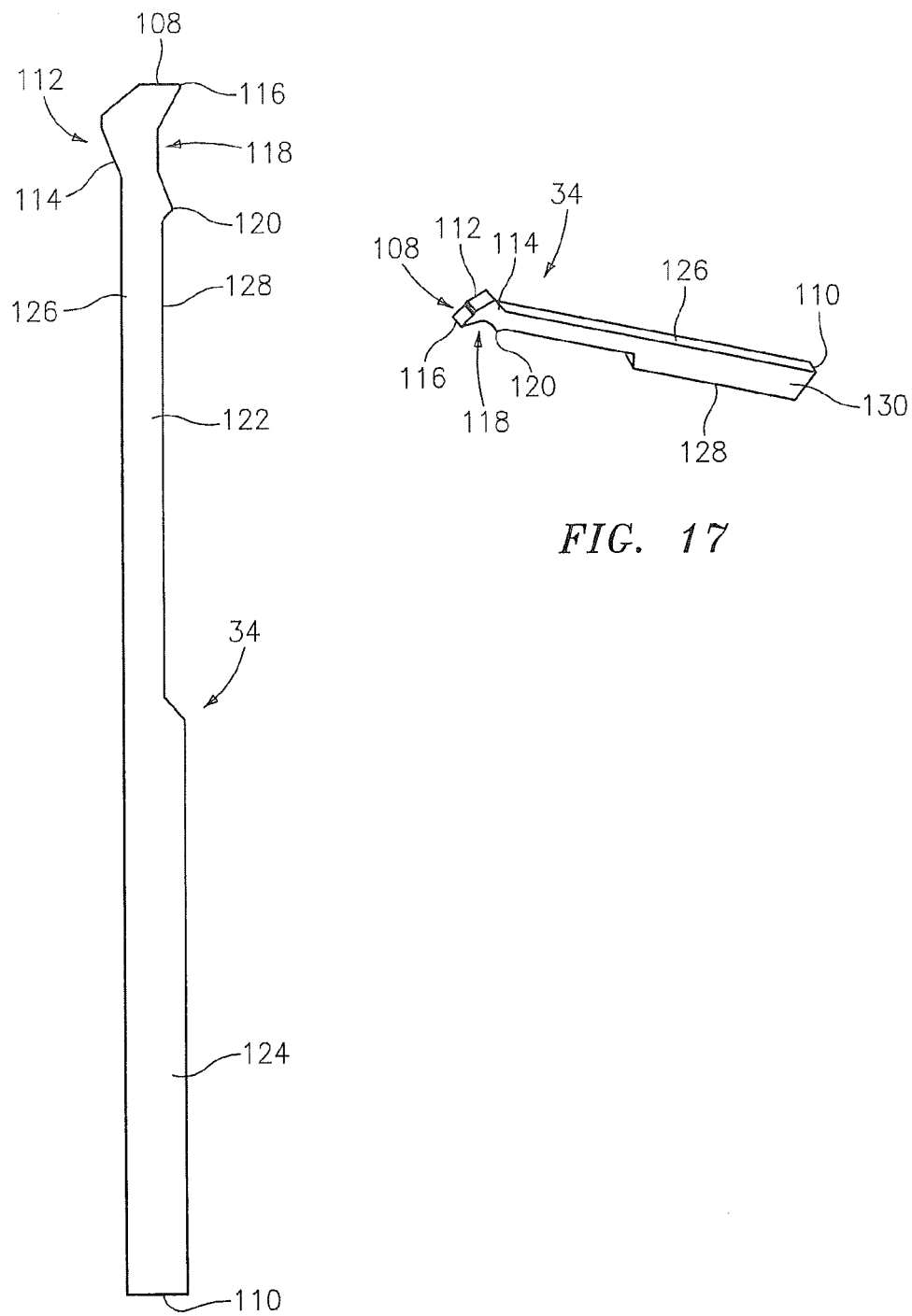
FIG. 16 shows a side plan view of the hammer element for the cutting and crimping device of FIG. 1.
FIG. 17 shows a perspective view of the hammer element of FIG. 16.

Turning now to FIGS. 16-17, the hammer element 34 is shown. The hammer element 34 includes a distal end 108 and a proximal end 110. The distal end 108 includes the hammer head 112. The hammer head 112 preferably includes a first camming surface 114 which engages with a camming surface on the tip 40 as will be further described. The first camming surface 114 is located on a first side 126 of the hammer element 34. The first camming surface 114 and the first side 126 form an obtuse angle as shown. Located on the second side 128 of the hammer element 34 is a ferrule engaging edge 116. An indent 118 may separate the ferrule engaging edge 116 and an edge 120. Alternatively edge 120 may be removed and replaced with a smooth continuous edge, continuous with second side 128. The hammer element 34 includes a central portion 122 of a selected width which is smaller in width than a proximal portion 124. The smaller width of the central portion 122 allows movement of the hammer head 112 within the tip 40. Each of the first side 126 and second side 128 may comprise a series of planar surfaces as shown in FIG. 17, with planar sides 130 connecting the first and second sides 126, 128. Thus, the hammer element 34 preferably comprises a rectangular cross-section. As shown in FIG. 1, the proximal end 110 of the hammer element 34 is mounted to the distal end 36 of the central rod 30.

Figure 18:
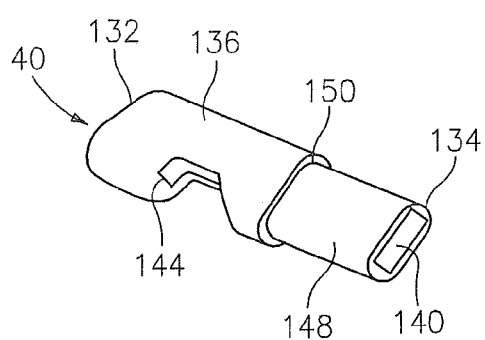
FIG. 18 shows a perspective view of the tip for the cutting and crimping device of FIG. 1.
Figure 19:
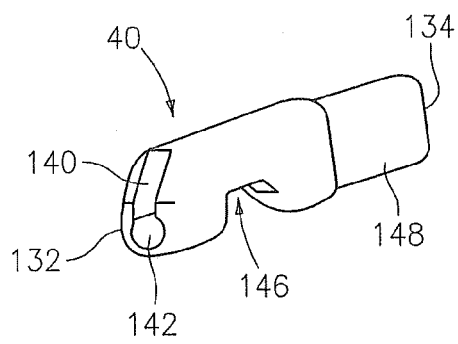
FIG. 19 shows another perspective view of the tip of FIG. 18.
Figure 20:
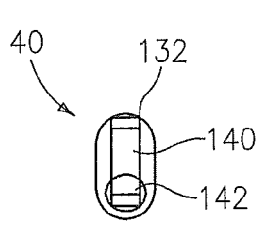
FIG. 20 shows a distal plan view of the tip of FIG. 18.
Figure 21:
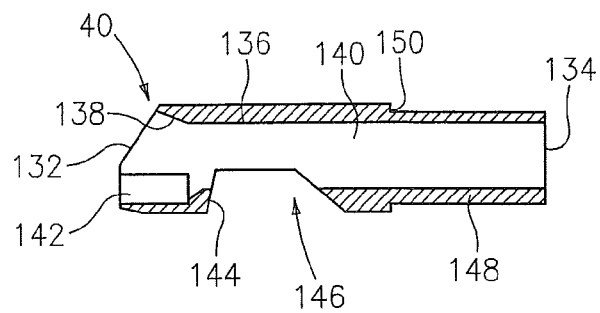
FIG. 21 shows a cross-sectional interior view of the tip of FIG. 18.

Turning now to FIGS. 18-21, tip 40 is shown in detail. Tip 40 has a distal end 132 and a proximal end 134. The distal end 132 includes a hammer head receiving portion 136 which includes a second camming surface 138 (shown in FIG. 21), which abuts with the first camming surface 114 of the hammer head 34 during retraction of the hammer element within the device 10. The second camming surface 138 forms part of a wall of the opening 140 of the tip 40. The opening 140 preferably extends the length of the tip 40 and has a rectangular cross section (as shown in FIG. 18) throughout most of the tip 40 for receiving the rectangularly shaped hammer element 34. The distal end 132 of the tip 40 further includes a ferrule accepting opening 142 which shares open space with the opening 140. Thus, the opening at the distal end 132, as shown in FIGS. 19 and 20 is generally key-hole shaped. Proximal the ferrule accepting opening 142 is a cutting edge 144 formed on an inner wall of the tip 40 for cutting the suture material as will be further described below. Adjacent the cutting edge 144 is an aperture 146 within the tip 40. The aperture 146 allows the suture material to be threaded through the ferrule 42 from the distal end 132 and exit the aperture 146. The tip 40 preferably includes a proximal portion 148 having a reduced width. A wall 150 is formed between the proximal portion 148 and the hammer head receiving portion 136.

Figure 22:
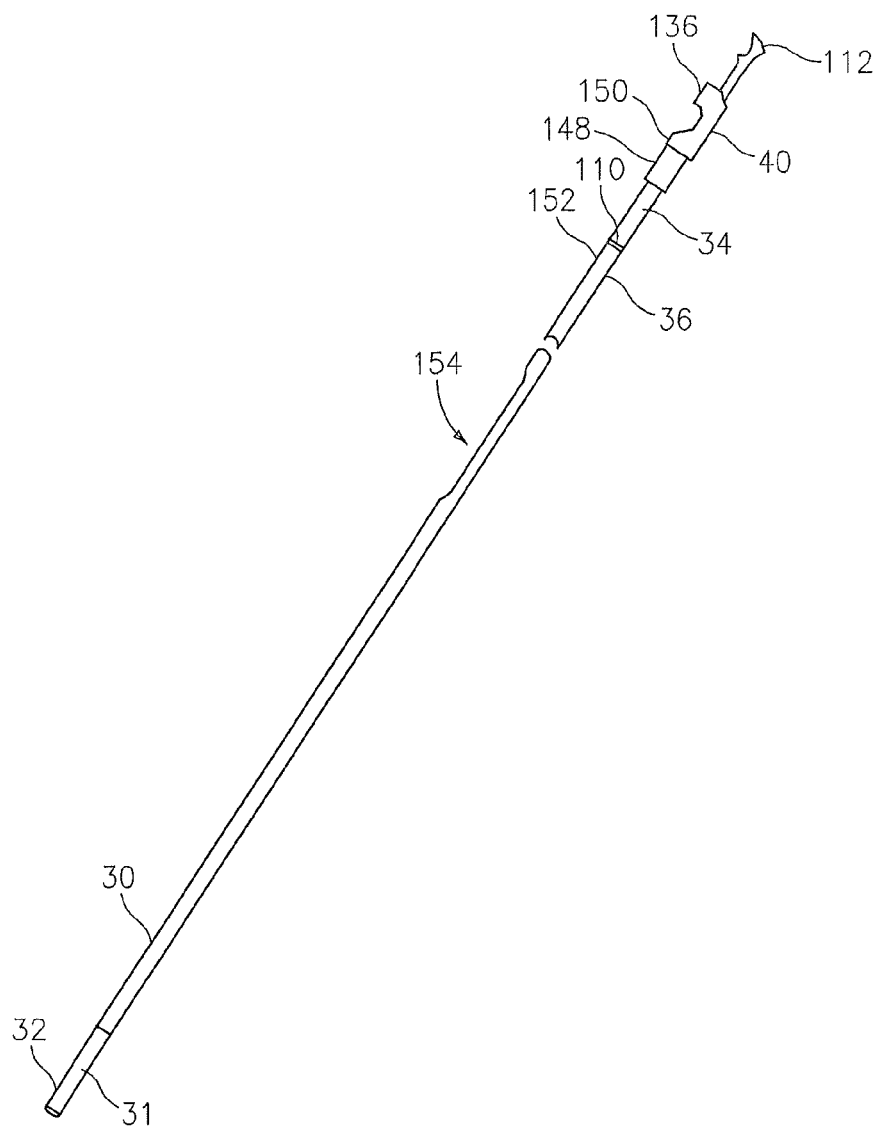
FIG. 22 shows a side plan view of the central rod, hammer element, and tip of the cutting and crimping device of FIG. 1.
Figure 23:
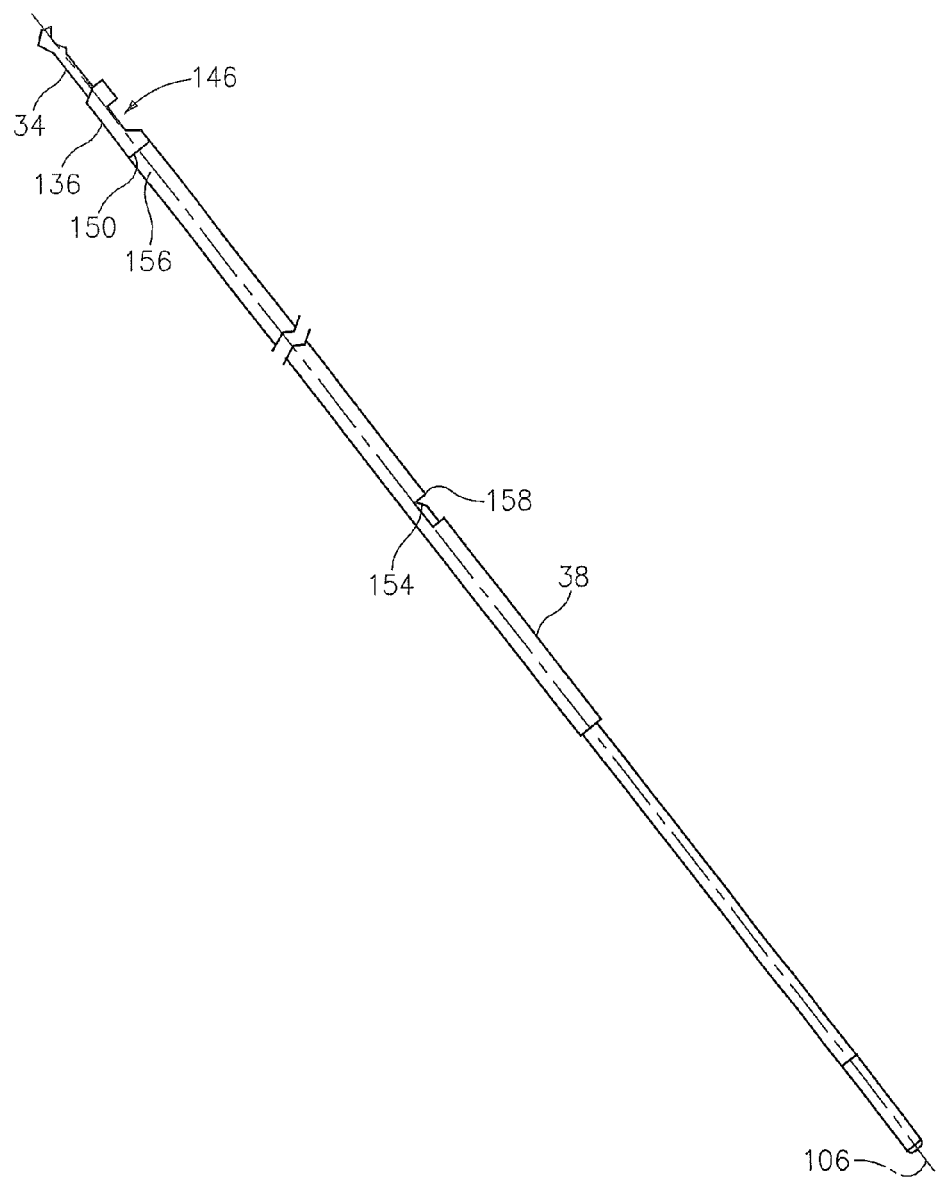
FIG. 23 shows a side plan view of the central rod, hammer element, tip, and tubular portion of the cutting and crimping device of FIG. 1.

Turning now to FIG. 22, the distal end 36 of central rod 30 is shown welded to the proximal end 110 of the hammer element 34 at area 152. Notch 154 is shown within the rod 30. Then, the tip 40 is installed upon the hammer element 34. Turning to FIG. 23, the tubular portion 38 is shown welded or otherwise secured to the tip 40 at or about area 156. The tubular portion 38 overlaps the proximal portion 148 of the tip 40 and abuts the wall 150, so that preferably a smooth continual surface is provided between the tubular portion 38 and the tip 40. Notch 158 within tubular portion 38 coincides with notch 154 in the central rod 30. An anti-rotation feature is provided using the aligned notches 154, 158 during assembly by placing a pin, such as a square pin, into the notch area, thus preventing the rod 30 from rotating within the tubular portion 38. Longitudinal axis 106, which also runs through adjustment screw 28, extends generally through the central rod 30 and tubular portion 38.

Figure 24:
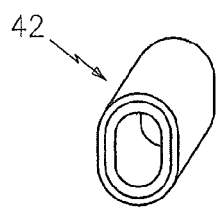
FIG. 24 shows a perspective view of a ferrule for use in the cutting and crimping device of FIG. 1.
Figure 25:
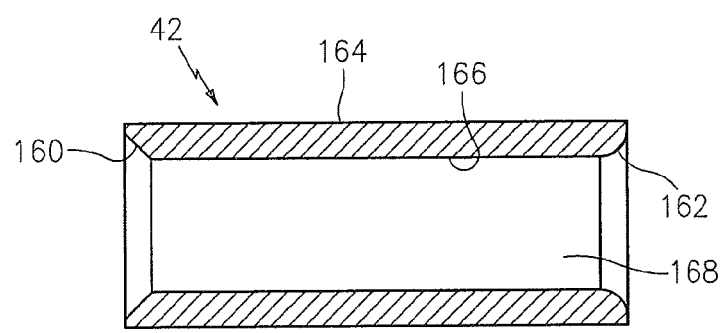
FIG. 25 shows a side cross-sectional view of the ferrule of FIG. 24.
Figure 33:
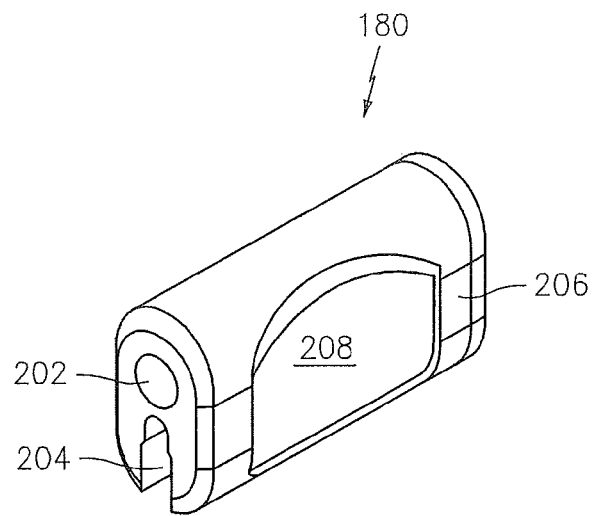
FIG. 33 shows a side perspective view of a cap for use in the suture loading assembly of FIG. 30.

FIGS. 24 and 25 show an exemplary ferrule 42 for use within the device 10, and more particularly for placement within the ferrule accepting opening 142 of the tip 40. The ferrule 42 includes a bore 168 which extends the length of the ferrule 42. Ferrule 42 preferably comprises an ovalized outer surface 164. The inner surface 166 of the ferrule 42 will contact the suture material upon compression, as will be described below. The ferrule 42 preferably comprises chamfered ends 160 and 162. The ends may be angled as shown by end 160 or more preferably rounded as shown by end 160. The ferrule 42 is preferably manufactured without burrs of any sort. The material selected for ferrule 42 is preferably annealed titanium, but may be formed from another deformable biocompatible material, such as another non-bioabsorbable material. Alternatively, the ferrule 42 may be formed from a bioabsorbable polymer.

FIGS. 26-29 describe how the hammer element 34 and tip 40 cooperate to compress the ferrule 42, secure the suture threads therein, and cut the suture thread ends. The ferrule 42 is shown positioned within the ferrule accepting opening 142 and the suture threads 170 have been threaded through the ferrule 42 and exit the aperture 146 of the tip 40. FIG. 26 shows the hammer head 112 positioned within the tip 40 such that the first camming surface 114 abuts the second camming surface 138. In this initial position, the ferrule engaging edge 116 may abut the ferrule 42 and provide a slight compression of the ferrule 42 for retaining the ferrule 42 within the ferrule accepting opening 142. Turning now to FIG. 27, as the hammer element 34 is drawn in the direction indicated by arrow 172, the hammer head 112 draws the first camming surface 114 along the second camming surface 138. In doing so, the hammer head 112 is brought closer to the ferrule 42 such that the ferrule engaging edge 116 begins to crimp or compress the ferrule 142. Turning to FIG. 28, with the hammer element 34 continually drawn in the direction indicated by arrow 172, the first camming surface 114 is no longer in contact with the second camming surface 138, but the first side 126 abuts the inner surface of the opening 140 within tip 40 such that the ferrule engaging edge 116 continues to crimp the ferrule 42. As shown in FIG. 29, after the hammer element 34 has been moved in the direction indicated by arrow 172 to completely crimp the ferrule 42, the ferrule engaging edge 116 moves towards the cutting edge 144 of the tip 40 until the suture threads 170 are trapped between the hammer head 112 and the cutting edge 144. A small amount of pressure from the hammer head 112 upon the cutting edge 144 will release the ends of the suture threads 170 as shown. Thus, the ferrule 42 is crimped and the suture ends are cut in one step. Additionally, the hammer element 34 does not contain the cutting edge, and therefore there is no risk of providing sharp edges to the ferrule 42 which will remain in the suture location.

Figure 34:
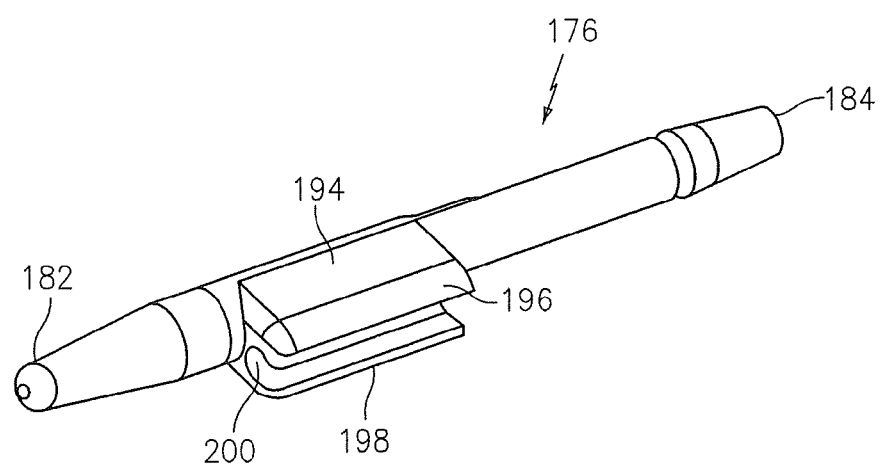
FIG. 34 shows a side perspective view of a body for use in the suture loading assembly of FIG. 30.
Figure 35:
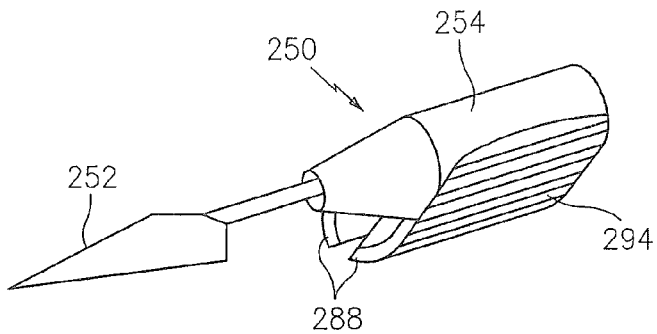
FIG. 35 shows a side perspective view of another embodiment of a suture loading assembly.
Figure 36:
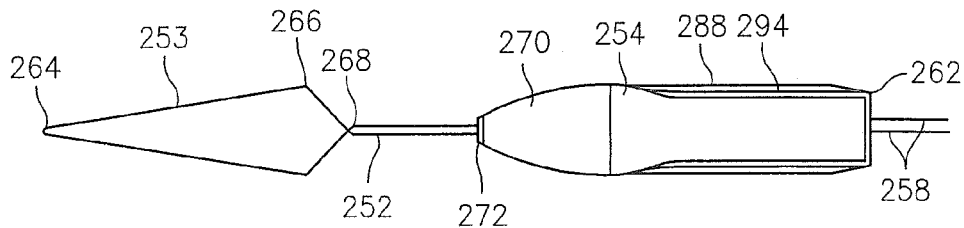
FIG. 36 shows a top plan view of the suture loading assembly of FIG. 35.
Figure 37:
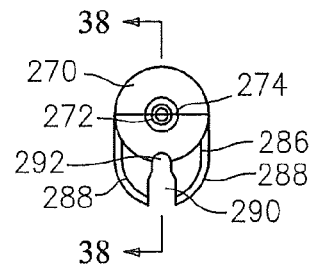
FIG. 37 shows a front plan view of the suture loading assembly of FIG. 35.

FIGS. 30-34 show one embodiment of a suture loading assembly 174 for assisting an operator in threading the suture threads 170 through the ferrule 42 after a suturing operation and before a suture securing operation. The suture loading assembly 174 preferably includes a body 176 from which extends a flexible loop 178, preferably made from suture material 186 or wire, such as stainless steel wire, and a cap 180. The body 176, as shown in FIG. 34, includes a distal end 182 from which the loop 178 exits, and a proximal end 184. The body 176 further preferably includes a bore 188 (FIG. 31) containing the suture material 186 from which the loop 178 is formed. As further shown in FIG. 31, the body 176 further preferably comprises a step 190 for abutting with a stopping surface 192 within the cap 180. Additionally, the body 176 further includes an attaching member 194, which may have a clip-like shape as shown with a pair of legs 196, 198. The legs 196 and 198 preferably define a rounded receiving pocket 200 for receiving the tubular portion 38.

Because of the small size of the tubular portion 38, and thus the body 176, the suture loading assembly 174 further preferably includes the cap 180 for easy grasping and operating by an operator. The cap 180 includes openings 202 and 204 for receiving the body 176 and attaching member 194. The cap 180 further preferably includes sides 206 which have indents 208 for ease in grasping.

The suture loading assembly 174 is preferably pre-assembled upon the device 10 by the manufacturer. During assembly, the suture loading assembly 174 is preferably secured to the tubular portion 38 by inserting the tubular portion 38 into the opening 204 of the cap 180 and snapping the attaching member 194 onto the tubular portion 38. The loop 178 (which may be much longer than what is shown) may then be pushed into the opening 146 in the tip 40 and threaded through the ferrule 42 which is preloaded within the tip 40. Thus, a portion of the loop 178 will remain extended through the ferrule 42 and out the distal end 132 of the tip 40. Alternatively, the loop 178 could be threaded through the ferrule 42 in the manner described and then the suture loading assembly could be secured to the tubular portion 38.

When a suturing operation has been completed, and it is time to utilize the crimping and cutting device 10 for securing the suture, the ends of the suture material 170 may be simply threaded through the large opening provided in the loop 178. Then, the operator may grasp the cap 180, such as at indents 208, and then the operator may pull the suture loading assembly 174 in a proximal direction, towards the handle assembly 12. In doing so, the loop 178, which is flexible and collapsible, will pull the suture material 170 through the ferrule 42 and out the opening 146 in the tip 40. Because the suture material 170 is likely to be wet and slippery following the suture operation, the ability to thread the suture material 170 through the ferrule 42 using the suture loading assembly 174 eliminates any tedious operational steps.

Turning now to FIGS. 35-38, another embodiment of a suture loading assembly is shown. The suture loading assembly 250 is similar in use to the suture loading assembly 174, but embodies a slightly different design. The suture loading assembly 250 includes a wire loop 252 made of wire 253, a body 254, and a plug 256. During assembly, ends 258 of wire loop 252 may be trimmed at location 260 after installing plug 256 so that the wire loop 252 ends flush with a proximal end 262 of the body 254. The wire loop 252 preferably includes a tapered distal end 264, a widest portion 266, and a cross-over portion 268 where the wire 253 crosses over itself prior to running parallel into the body 254.

Figure 38:
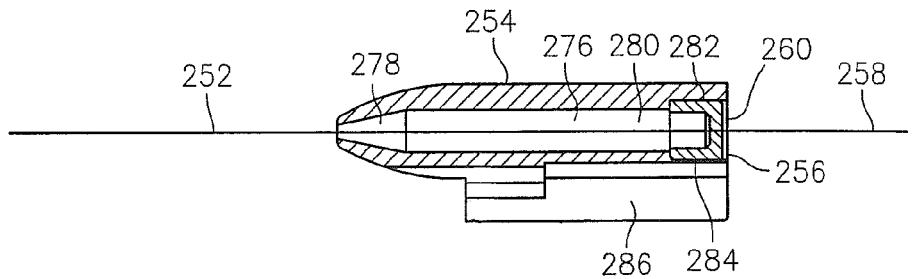
FIG. 38 shows a side cross-sectional view of the suture loading assembly of FIG. 35 taken along line 38-38 within FIG. 37.

The body 254 includes a tapered nose section 270 having a distal end 272 and an opening 274. The opening 274 receives the wire 253 of the wire loop 252. As shown in FIG. 38, the opening 274 leads to a longitudinal bore 276 having a main bore 280 with a first inner diameter, distal tapered section 278 having a smaller inner diameter than the first inner diameter, and a proximal bore 282 having a second inner diameter slightly larger than the first inner diameter, such that a stopping surface 284 is provided within the bore 276. During assembly, the plug 256 is inserted into the proximal end 262 of the body 254 for retaining the wire loop 252 within the body 254.

The body 254 further preferably includes an integral attaching member 286 which includes a pair of clip-like legs 288 separated by a slot 290 having a rounded end 292 for receiving the tubular portion 38. Each leg 288 further preferably includes an indented area 294 for ease in grasping.

As with the suture loading assembly 174, the suture loading assembly 250 is preferably pre-assembled upon the device 10 by the manufacturer. During assembly, the suture loading assembly 250 is preferably secured to the tubular portion 38 by inserting the tubular portion 38 into the slot 290 and snapping the attaching member 286 onto the tubular portion 38 with the tubular portion 38 residing in the rounded end 292 of the slot 290. The wire loop 252, which is sufficiently flexible, may be pushed into the opening 146 in the tip 40 and threaded through the ferrule 42 which is preloaded within the tip 40. Thus, a portion of the wire loop 252 will remain extended through the ferrule 42 and out the distal end 132 of the tip 40. Preferably, the wire loop 252 is preformed such that upon its exit through the ferrule 42, it will begin to open up automatically thus creating a stable opening, as opposed to suture material in which the opening may have to be created by separating the thread used in the loop 178 in the suture loading assembly 174. Alternatively, the wire loop 252 could be threaded through the ferrule 42 in the manner described and then the suture loading assembly 250 could be secured to the tubular portion 38. The ends of suture material 170 may be threaded through the large opening provided in the wire loop 252, and the operator may grasp the indented areas 294 and pull the suture loading assembly 252 in a proximal direction, towards the handle assembly, for pulling the suture material 170 through the ferrule 42 as previously described with the operation of the suture loading assembly 174.

Figure 39:
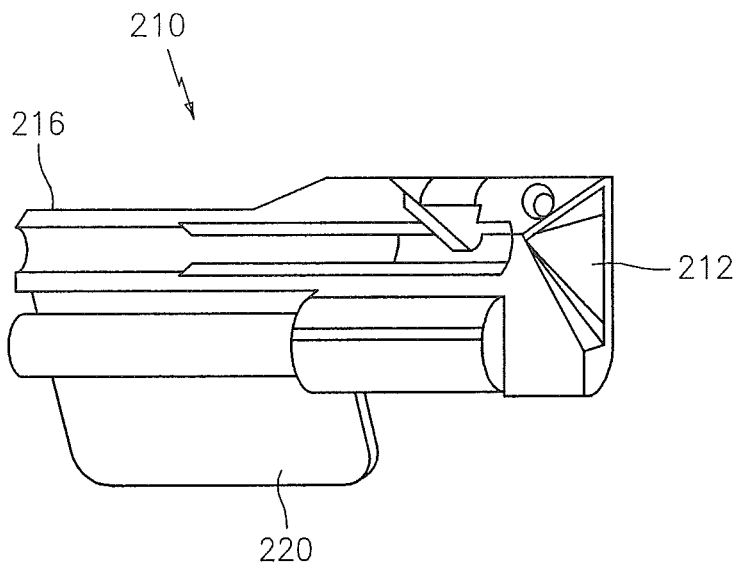
FIG. 39 shows a side perspective view of a half of another embodiment of a suture loading assembly; and, FIG. 40 shows a side perspective view of another half of the suture loading assembly of FIG. 39.
Figure 40:
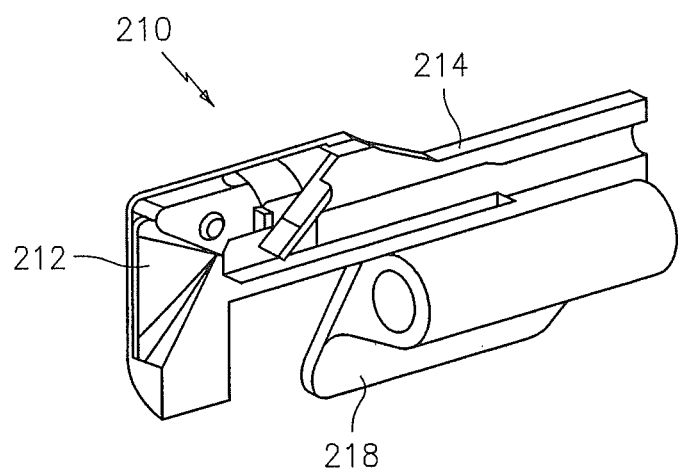

FIGS. 39 and 40 show an alternate embodiment of a suture loading assembly 210, where halves of the suture loading assembly 210 are depicted in FIGS. 39-40. Looking at the suture loading assembly from a distal location, i.e. from the funnel 212, FIG. 40 shows a left half 214 and FIG. 39 depicts a right half 216. The two halves 214, 216 preferably snap onto the distal end of the device 10 for threading of the ferrule 42. The suture material 170 may be threaded through a funnel 212 created by a joining of the two halves 214, 216. Then, the threads 170 would go directly into the ferrule 42 after being pushed into the funnel 212. After the ferrule 42 is threaded, the wings 218, 220 may be squeezed together to release the suture loading assembly 210 from the distal end of the device 10. Thus, with the suture material 170 threaded through the ferrule 42, the device 10 may be inserted near the suture location (the area where the body was closed by the suture material 170) to secure the ferrule 42 upon the suture material 170.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A suture loading assembly for threading suture material through a surgical instrument, the suture loading assembly comprising:
    a body,
    an attaching member extending from the body for attaching the body on an exterior portion of the surgical instrument, the attaching member including a pair of legs separated by a slot that is configured to receive a tubular portion of said surgical instrument;
    a collapsible, flexible loop extending from a distal end of the body, wherein the flexible loop in a first position, is provided through an opening in the tubular portion of the surgical instrument, and in a second position is provided at least partially retracted from said opening, wherein in said second position, said suture material is at least partially provided within said surgical instrument opening; and
    a cap surrounding a portion of the body, the cap including at least one of: finger grips; and openings for receiving the body and the attaching member.

2. The suture loading assembly of claim 1 wherein the body includes a bore from which the loop extends.

3. The suture loading assembly of claim 1 wherein an inner portion of each leg is curved to accept the tubular portion of the surgical instrument, wherein the attaching member is slidable along the the tubular portion of the surgical instrument.

4. The suture loading assembly of claim 1, wherein the cap includes finer grips, and the finger grips are indents in sides of the cap.

5. The suture loading assembly of claim 1 wherein the loop is made from wire.

6. The suture loading assembly of claim 5 further comprising a plug inserted within a proximal end of the body for retaining the wire within the body.

7. In combination, a suture securing instrument and a suture loading assembly, the suture securing instrument comprising:
    an elongated tubular portion having a distal end and a proximal end, the distal end including a ferrule accepting opening, the proximal end attached to a handle assembly;
    the suture loading assembly comprising:
    a body,
    an attaching member extending from the body for attaching the body on an exterior portion of the elongated tubular portion of the suture securing instrument, the attaching member including a pair of legs separated by a slot that is configured to receive the tubular portion of said suture securing instrument; and,
    a collapsible, flexible loop extending from a distal end of the body, wherein the flexible loop in a first position, is provided through an opening in a ferrule within said ferrule accepting opening, and in a second position is provided at least partially retracted from said ferrule, wherein in said second position, suture material is at least partially provided within said ferrule.

8. The combination of claim 7 wherein the loop is threaded through the ferrule accepting opening.

9. The combination of claim 7 wherein the attaching member is slidable along the tubular portion of the suture securing instrument.

10. The combination of claim 9 wherein an inner portion of each leg is curved to accept the tubular portion of the suture securing instrument.

11. The combination of claim 10 wherein an outer portion of each leg includes an indented area for providing a finger grip.

12. The combination of claim 7 wherein the suture loading assembly further comprises a cap surrounding the body and attaching member, the cap extending past the tubular portion.

13. The combination of claim 12 wherein the cap includes a pair of indents usable as finger grips.

14. The combination of claim 7 wherein the suture securing instrument further comprises an aperture in the elongated tubular portion, the aperture located proximally of the ferrule accepting opening, the flexible loop threaded through the aperture prior to threading through the ferrule accepting opening.

15. The combination of claim 14 further comprising a ferrule positioned in the ferrule accepting opening, the flexible loop threaded through the ferrule.

16. The combination of claim 7 wherein the loop is made from a preformed wire bent into a diamond shape.

17. A method of threading a suture securing instrument comprising:
   mounting a suture loading assembly having a body upon a tubular body portion of the suture securing instrument with an attaching member that extends from the body of the suture loading assembly to mount the assembly on an exterior portion of the tubular body portion of the suturing securing instrument, the attaching member including a pair of legs separated by a slot that is configured to receive the tubular body portion of said suture securing instrument; and,
   threading a collapsible, flexible loop extending from the suture loading assembly through a ferrule within a distal end of the suture securing instrument.

18. The method of claim 17 further comprising inserting suture material through the flexible loop.

19. The method of claim 18 further comprising pulling the flexible loop proximally until the suture material is threaded through the ferrule.

20. The method of claim 19 wherein pulling the flexible loop proximally comprises sliding the suture loading assembly proximally along the tubular body portion of the suture securing instrument.

21. A kit for securing suture material within a body of a patient, the kit comprising:
   a cutting and crimping device;
   a ferrule loaded into the cutting and crimping device; and,
   a suture loading assembly mounted on a tubular portion of the cutting and crimping device, the suture loading assembly comprising an attaching member, the attaching member including a pair of legs separated by a slot that is configured to receive the tubular portion of said cutting and crimping device, a collapsible, flexible loop extending from the suture loading assembly threaded through the ferrule.

* * * * *